US012710394B2

(12) United States Patent
Karajic et al.

(10) Patent No.: US 12,710,394 B2
(45) Date of Patent: Aug. 18, 2026

(54) ELECTROCHEMICAL APTAMER SENSOR MONOLAYER INCUBATION WITH IMPROVED STABILITY

(71) Applicant: University of Cincinnati, Cincinnati, OH (US)

(72) Inventors: Aleksandar Karajic, Cincinnati, OH (US); Zachary Lee Watkins, Cincinnati, OH (US); Jason Charles Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 263 days.

(21) Appl. No.: 18/686,623

(22) PCT Filed: Sep. 23, 2022

(86) PCT No.: PCT/US2022/044504
§ 371 (c)(1),
(2) Date: Feb. 26, 2024

(87) PCT Pub. No.: WO2023/049324
PCT Pub. Date: Mar. 30, 2023

(65) Prior Publication Data

US 2024/0377348 A1 Nov. 14, 2024

Related U.S. Application Data

(60) Provisional application No. 63/248,016, filed on Sep. 24, 2021.

(51) Int. Cl.
*G01N 27/327* (2006.01)
*G01N 33/543* (2006.01)

(52) U.S. Cl.
CPC ..... *G01N 27/3276* (2013.01); *G01N 27/3277* (2013.01); *G01N 33/5438* (2013.01)

(58) Field of Classification Search
None
See application file for complete search history.

(56) References Cited

U.S. PATENT DOCUMENTS

2019/0376987 A1 12/2019 Xiao et al.

FOREIGN PATENT DOCUMENTS

| | | |
|---|---|---|
| CN | 108490053 B | 11/2019 |
| CN | 107315044 B | 4/2020 |
| CN | 110632151 B | 8/2021 |
| WO | 2020082491 A1 | 4/2020 |

OTHER PUBLICATIONS

International Search Report and Written Opinion in International Patent Application No. PCT/US2022/044504, mailed Dec. 9, 2022, 14 pgs.

*Primary Examiner* — J. Christopher Ball
(74) *Attorney, Agent, or Firm* — Wood Herron & Evans LLP

(57) ABSTRACT

A method of fabricating an electrochemical aptamer sensor is provided. The method includes incubating an electrode including a sensing monolayer. The sensing monolayer includes at least a plurality of aptamers and at least one weakly bonded constituent. The method further includes removing the at least one weakly bonded constituent from the sensing monolayer by applying at least one perturbation mechanism to the sensing monolayer while incubating the electrode.

12 Claims, 12 Drawing Sheets

5 mM MCH (2h)
1 mM MCH (overnight)
Current (μA)
-2.0
-1.8
-1.6
-1.4
-1.2
-1.0
-0.8
-0.6
-0.4
-0.2
-0.6
-0.5
-0.4
-0.3
-0.2
-0.1
Potential (V)/ vs Ag/AgCl (3M KCl)

ELECTROCHEMICAL APTAMER SENSOR MONOLAYER INCUBATION WITH IMPROVED STABILITY

CROSS REFERENCE TO RELATE APPLICATIONS

The present application is an International Patent Application which claims priority to, and the benefit of the filing date of, U.S. Ser. No. 63/248,016, titled "Electrochemical Aptamer Sensor Monolayer Incubation with Improved Stability," which was filed Sep. 24, 2021, the disclosure of which is hereby incorporated herein by reference in its entirety.

FIELD OF INVENTION

The present disclosure relates to sensor devices, specifically to electrochemical aptamer sensor devices and methods of making electrochemical aptamer sensor devices.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Electrochemical aptamer sensors can identify the presence and/or concentration of an analyte of interest via the use of an aptamer sequence that specifically binds to the analyte of interest. These sensors include aptamers attached to an electrode, wherein each of the aptamers has a redox active molecule (redox tag) attached thereto. The redox couple can transfer electrical charge to or from the electrode. The aptamers can be considered a sensing monolayer, or a constituent of a sensing monolayer. Such sensing monolayers may include other constituent components-such as materials that create a blocking layer as part of the sensing monolayer. Thus, one embodiment of a sensing monolayer may comprise aptamers and blocking layer molecules. When an analyte binds to the aptamer, the aptamer changes its conformation, bringing the redox couple closer to or further from, on average, the electrode. This results in a measurable change in electrical current that can be translated to a measure of presence or concentration of the analyte. When used in this manner, then, aptamers are an example of an affinity-based biosensor. The blocking layer portion of the sensing monolayer (1) ensures the aptamer moves freely and properly in its conformation change upon analyte bonding, and (2) reduces electrical background current (including oxygen reduction current), which would otherwise wash-out the measured signal from the aptamer and redox tag.

An unresolved challenge for aptamers occurs during the initial "burn in" of the aptamer sensor due to loss of components of the sensing monolayer that are poorly bonded to the electrode. For example, one or more of the aptamers and other materials (e.g., molecules that are the blocking layer components) that comprise the sensing monolayer may not bond, or may only weakly bond to the electrode during fabrication (such bonding may occur during a process of incubation of the electrode with the various components of the sensing monolayer). Weakly bonded constituents include those that may be physiosorbed, attached at rough high electric field points on the electrode, attached at other weak points on the electrode, oriented with other components of the sensing monolayer such that they are less stable, etc. Thus, once the sensing device is fabricated, it may rapidly lose portions of blocking layer (and/or aptamers) that are only weakly bonded. As these portions are lost, the overall performance of the device is reduced. Therefore, what is needed is an electrochemical aptamer device or method that is more robust than existing techniques to ensure that the monolayer is more uniformly or robustly bonded to the electrode that it is incubated onto (in order to prevent the degradation of the sensing monolayer with the resultant reduction in performance of the device).

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sensing technology into proximity with sample fluids containing at least one analyte of interest to be measured.

Embodiments of the disclosed invention are directed to aptamer sensors with improved stability of the incubated sensing monolayer. For example, a method of fabricating an electrochemical aptamer sensor is provided. The method includes incubating an electrode with components that have the ability to constitute a sensing monolayer. The incubating of these components with the electrode results in a sensing monolayer (e.g., aptamers and blocking layer materials) forming and attaching to a surface of the electrode. However, during this incubation and attachment of sensing monolayer to electrode, one or more constituent component may result in being weakly bonded to the electrode. And so, in one embodiment, the sensing monolayer includes at least a plurality of aptamers and at least one weakly bonded constituent. The method then further includes removing the at least one weakly bonded constituent from the sensing monolayer by applying at least one perturbation mechanism to the sensing monolayer while incubating the electrode.

In a related embodiment, the perturbation mechanism is selected from the group consisting of an electrical mechanism, a mechanical mechanism, a chemical mechanism, a thermal mechanism, and a combination thereof.

In a related embodiment, the sensing monolayer further includes a blocking layer.

In a related embodiment, the blocking layer includes a material that is an alkythiolate.

In a related embodiment, the plurality of aptamers each include at least one redox tag, and applying the perturbation mechanism decreases a normalized current measured as a peak signal from the redox tag versus a background current decreases over 24 hours by an amount selected from the group consisting of less than 3%, less than 5%, less than 10%, less than 20%, and less than 40%.

In a related embodiment, the plurality of aptamers are at least one of greater than 30%, greater than 60%, greater than 90%, or greater than 95% chemically attached to the electrode compared to a total aptamer on the electrode surface via both chemical and physiosorbed attachment.

Sensor devices are also included in the disclosure. For example, an electrochemical aptamer sensor is provided. The electrochemical aptamer sensor includes an electrode with a sensing monolayer. The sensing monolayer includes a plurality of molecules forming the sensing monolayer, and the plurality of molecules is attached to the electrode at an electrode surface. The plurality of molecules attached at the electrode surface may be either chemically or physiosorbed, and of a total of the plurality molecules attached at the electrode surface at least greater than one of 60%, 90%, 95% are chemically attached.

In a related embodiment, at least a portion of the plurality molecules are aptamers.

In a related embodiment, at least a portion of the plurality of molecules form a blocking layer.

In another embodiment, an electrochemical aptamer sensor is provided. The electrochemical aptamer sensor includes an electrode having an electrode surface. The electrochemical aptamer sensor further includes a sensing monolayer, the sensing monolayer including at least a plurality of molecules forming the sensing monolayer, the sensing monolayer attached to the electrode surface. The plurality of molecules attached to the electrode surface may be either weakly bonded or strongly bonded to the electrode surface, and, of the plurality of molecules, at least one of less than 40%, less than 20%, less than 10% or less than 5% of the sensing monolayer are weakly bonded to the electrode surface.

In a related embodiment, the molecules are aptamers.

In a related embodiment, the molecules form a blocking layer.

BRIEF DESCRIPTION OF THE DRAWINGS

The objects and advantages of the disclosed invention will be further appreciated in light of the following detailed descriptions and drawings in which.

DEFINITIONS

Figure 1A:
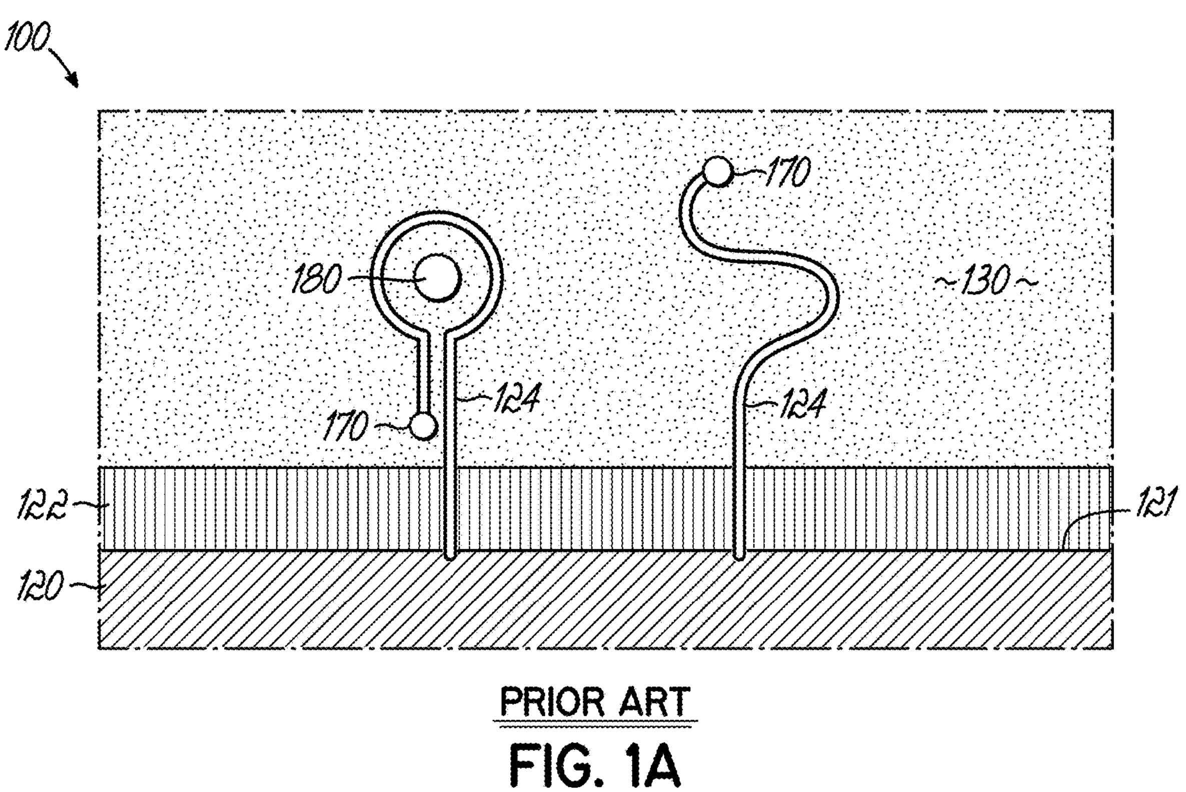
FIG. 1A is a schematic of a conventional prior art sensor device and a sample fluid included in the conventional prior art sensor device.

As used herein, the term "about," when referring to a value or to an amount of mass, weight, time, volume, pH, size, concentration, or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "aptamer" means an oligonucleotide molecule that undergoes a conformation change as an analyte binds to the molecule, and which satisfies the general operating principles of the sensing method as described herein. Such molecules are, e.g., natural or modified DNA, RNA, or XNA oligonucleotide sequences, spiegelmers, peptide aptamers, and affimers. Modifications may include substituting unnatural nucleic acid bases for natural bases within the aptamer sequence, replacing natural sequences with unnatural sequences, or other suitable modifications that improve sensor function. Aptamers can be optical or electrochemically detectable in nature using attached fluorescent and optical quencher tags as used in molecular beacons, or for example redox molecule tagged as is used in electrochemical aptamer-based sensors. Aptamers can function as a single nucleotide strand or as two or more strands whose conformational change is induced upon biding with molecular targets.

As used herein, the term "sensing monolayer" means at least a plurality of aptamers on a working electrode, which may also include a plurality of molecules or mixtures of molecules that form a blocking layer. Example "blocking layer" molecules may include, for example, alkythiolates such as mercaptohexanol, hexanethiol, peptides, and other suitable materials grafted onto the electrode surface.

As used herein, "weakly bonded constituents of the sensing monolayer" are those that can be tested using methods described herein and which will desorb from the working electrode within the first 24 hours of operation of a sensor. Weakly bonded constituents include those that may be physiosorbed, attached at rough high electric field points on the electrode, attached at other weak points on the electrode, oriented with other components of the sensing monolayer such that they are less stable (e.g. mercaptohexanol weakly standing in isolation vs. being tightly surrounded by other stabilizing mercaptohexanol molecules), or other constituent bonding mechanisms that present a weakly bonded configuration.

The devices and methods described herein encompass sensors and the use of sensors. A "sensor", as used herein, is a device that is capable of measuring the concentration of a target analyte in solution. As used herein, an "analyte" may be any inorganic or organic molecule, for example: a small molecule drug, a metabolite, a hormone, a peptide, a protein, a carbohydrate, a nucleic acid, an ion or any other composition of matter. The target analyte may comprise a drug. The drug may be of any type, for example, including drugs for the treatment of cardiac system, the treatment of the central nervous system, that modulate the immune system, that modulate the endocrine system, an antibiotic agent, a chemotherapeutic drug, or an illicit drug. The target analyte may comprise a naturally-occurring factor, for example a hormone, metabolite, growth factor, neurotransmitter, inflammatory mediators etc. The target analyte may comprise any other species of interest, for example, species such as pathogens (including pathogen induced or derived factors), nutrients, and pollutants, etc.

As used herein, the term "continuous sensing" simply means the device records a plurality of readings over time. Even a point-of-care testing device which provides a single data point can be considered a continuous sensing device if, for example, it is a 15 minute test, that operates by taking multiple data points over 15 minutes and averaging them to provide a single data measure.

As used herein, the term "analyte" means any solute in a solution or fluid which can be measured using a sensor. Analytes can be small molecules, proteins, peptides, electrolytes, acids, bases, antibodies, molecules with small molecules bound to them, DNA, RNA, drugs, chemicals, pollutants, or other solutes in a solution or fluid.

As used herein, the term "sample fluid" means any solution or fluid that contains at least one analyte to be measured. Sample fluids could be interstitial fluid, river water, body fluids, food processing waste, or other sample fluids.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Certain embodiments of the disclosed invention include sensors as simple individual elements. It is understood that many sensors require two or more electrodes, counter electrodes, reference electrodes, or additional supporting technology or features which are not captured in the description herein. Sensors measure a characteristic of an analyte. Sensors are preferably electrical in nature, but may also include optical, chemical, mechanical, or other known biosensing mechanisms. Sensors can be in duplicate, triplicate, or more, to provide improved data and readings. Sensors may provide continuous or discrete data and/or readings. Certain embodiments of the disclosed invention show subcomponents of what would be sensing devices with more sub-components needed for use of the device in various applications, which are known (e.g., a battery, antenna, adhesive), and for purposes of brevity and focus on inventive aspects, such components may not be explicitly shown in the diagrams or described in the embodiments of the disclosed invention. For example, electrochemical aptamer sensors typically require separate working, counter, and reference electrodes, but the present invention simply focuses its discussion on the working electrode which is coupled to the sensing transducing bioreceptor element in the form of a mixed monolayer of aptamers and blocking molecules.

With reference to FIG. 1A, a conventional prior art sensor device 100 as placed initially in a sample fluid 130 such as interstitial fluid is shown. The sensor device 100 includes at least one working electrode 120 which includes a material such as gold, carbon, or other suitable electrode material. The sensor device 100 also includes at least one blocking layer 122 which includes a plurality of molecules such as mercaptohexanol or hexanethiol that bond to the electrode 120 through a formation of the gold-thiol bond, or a plurality of natural solutes such as amino acids, peptides, albumin, some of which may be found in blood for example, that can act as the blocking layer 122, or other suitable molecules. The specific species of molecules included in the blocking layer 122 may depend on the particular application of the sensor device 100, and on the choice of electrode 120 material. The sensor device 100 further includes at least one aptamer 124 that is responsive to binding to an analyte 180 and which contains a redox tag 170 such as methylene blue. FIG. 1A shows a generic example of the conventional sensing device 100. As shown in FIG. 1A, the aptamer 124 is a simple stem loop (hairpin) aptamer configured to bond to the analyte 180. The bonding of the aptamer 124 to the analyte 180 causes the stem loop to form and the redox current measured from the redox tag 170 to increase, as measured using square wave voltammetry or other suitable technique. In an absence of analyte 180 binding to the aptamer 124, the favorable stem loop conformation would not form, and the redox current would thus not increase. Thus, a measurement of electrical current from the redox tag 170 can be used to interpret changes in the amount of analyte 180 bonded to the aptamer 124, and accordingly related to, for example, the concentration of the analyte 180 in the sample fluid 130.

Figure 1B:
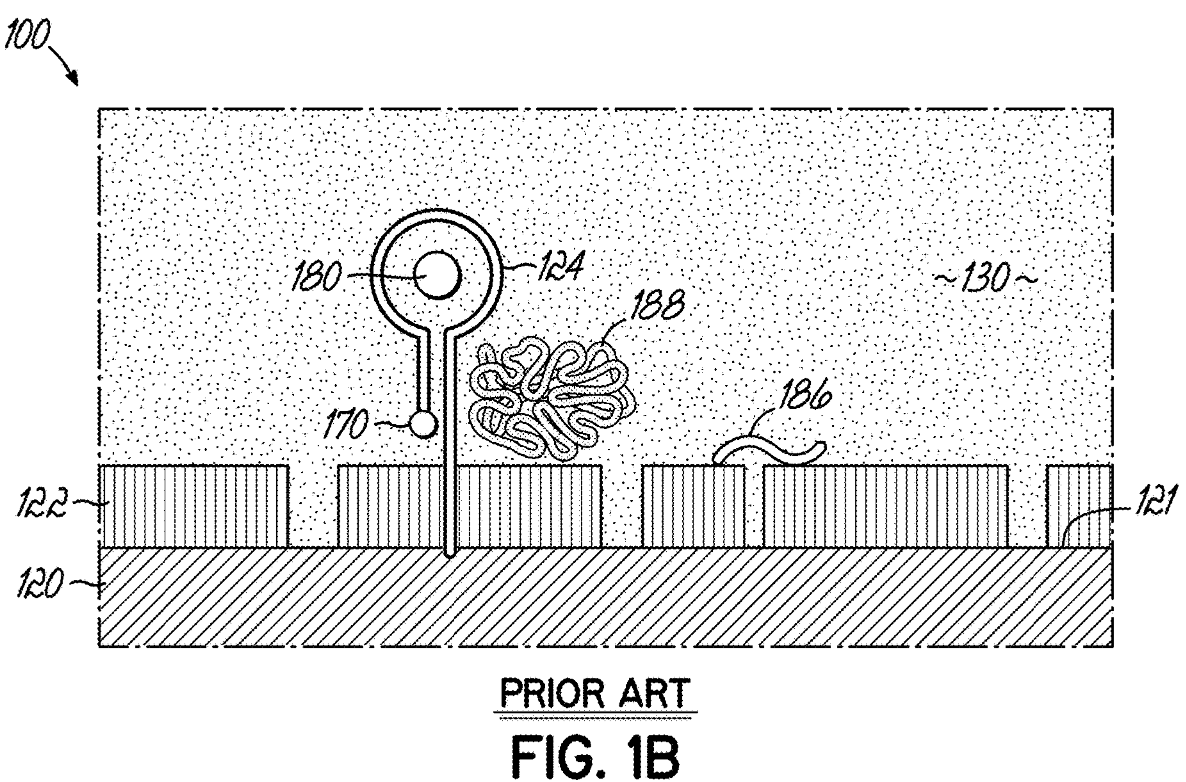
FIG. 1B is a schematic of a conventional prior art sensor device and a sample fluid included in the conventional prior art sensor device.
Figures 2A, 2B:
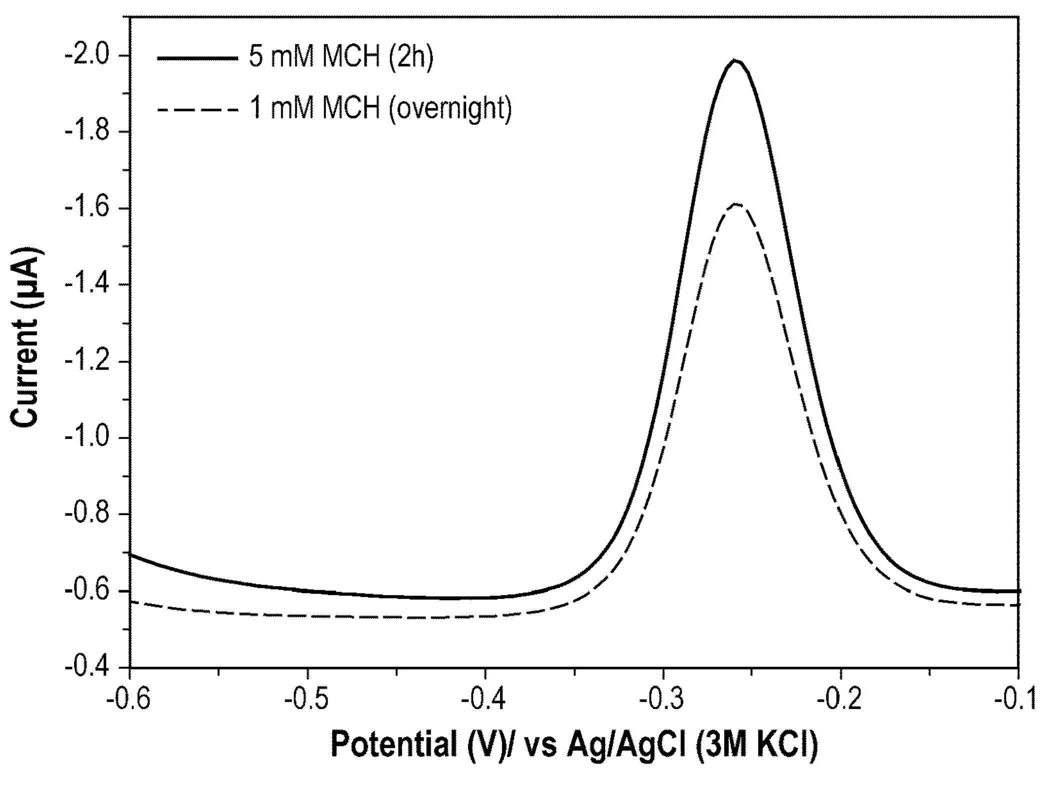
FIG. 2A is a graph showing potential versus current with a curve representing sensing devices incubated in 5 mM mercaptohexanol (MCH) for 2 hours and a curve representing sensing devices incubated in 1 mM MCH overnight.
FIG. 2B is a graph showing potential versus current with a curve representing sensing devices incubated in 5 mM MCH for 2 hours and a curve representing sensing devices incubated in 1 mM MCH overnight.
Figure 2C:
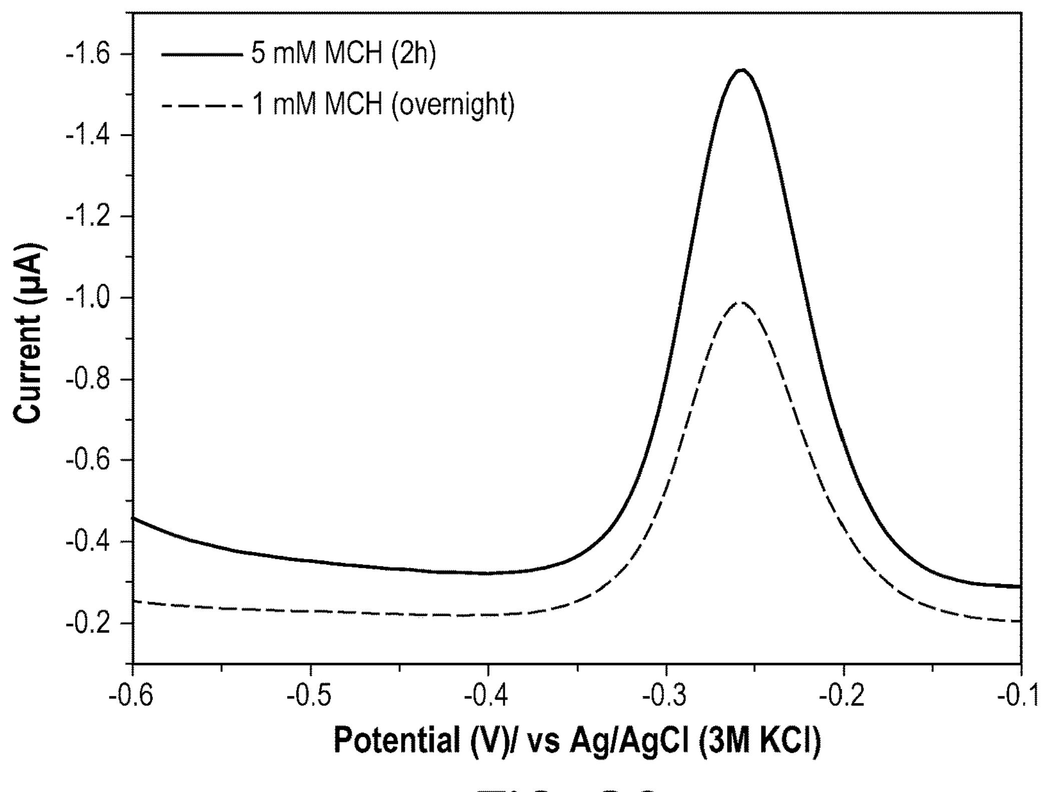
FIG. 2C is a graph showing potential versus current with a curve representing sensing devices incubated in 5 mM MCH for 2 hours and a curve representing sensing devices incubated in 1 mM MCH overnight.
Figure 2D:
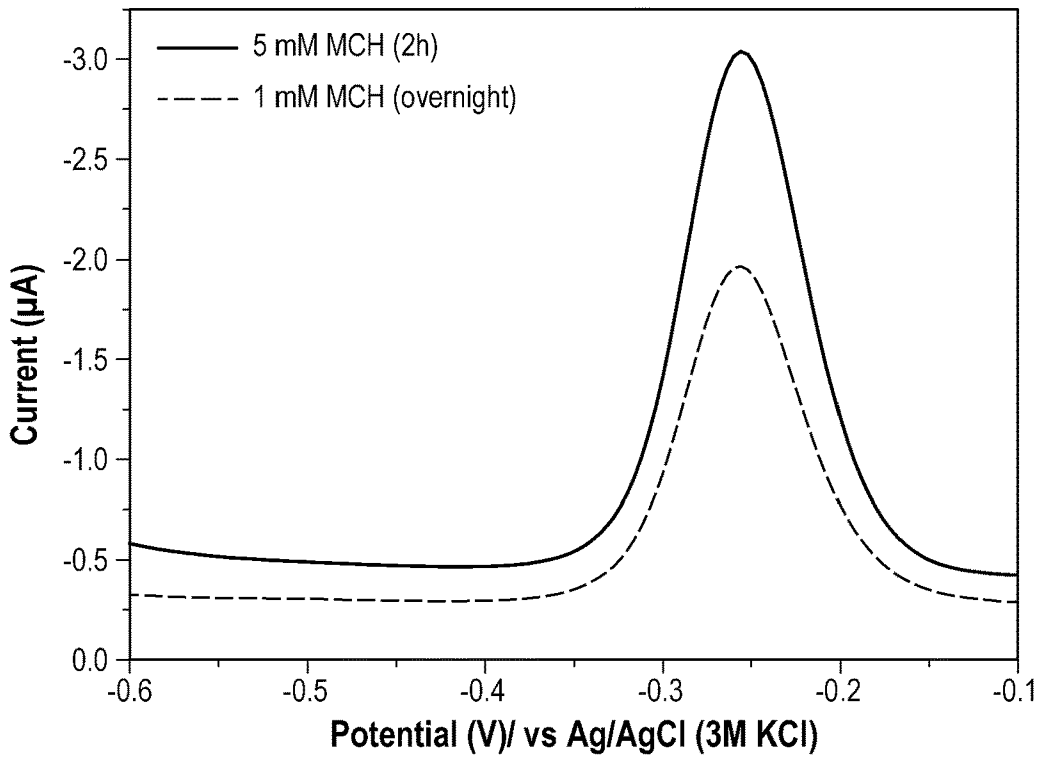
FIG. 2D is a graph showing potential versus current with a curve representing sensing devices incubated in 5 mM MCH for 2 hours and a curve representing sensing devices incubated in 1 mM MCH overnight.
Figure 3A:
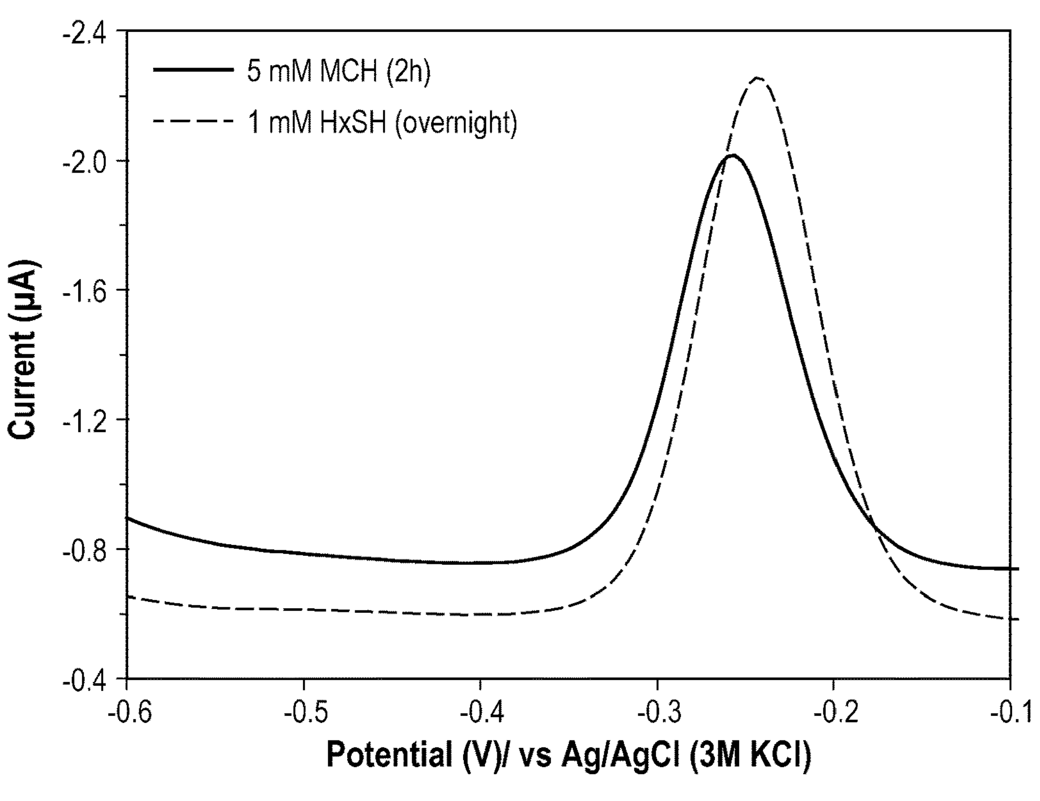
FIG. 3A is a graph showing potential versus current with a curve representing sensing devices incubated in 5 mM MCH for 2 hours and a curve representing sensing devices incubated in 1 mM hexanethiol (H×SH).
Figure 3B:
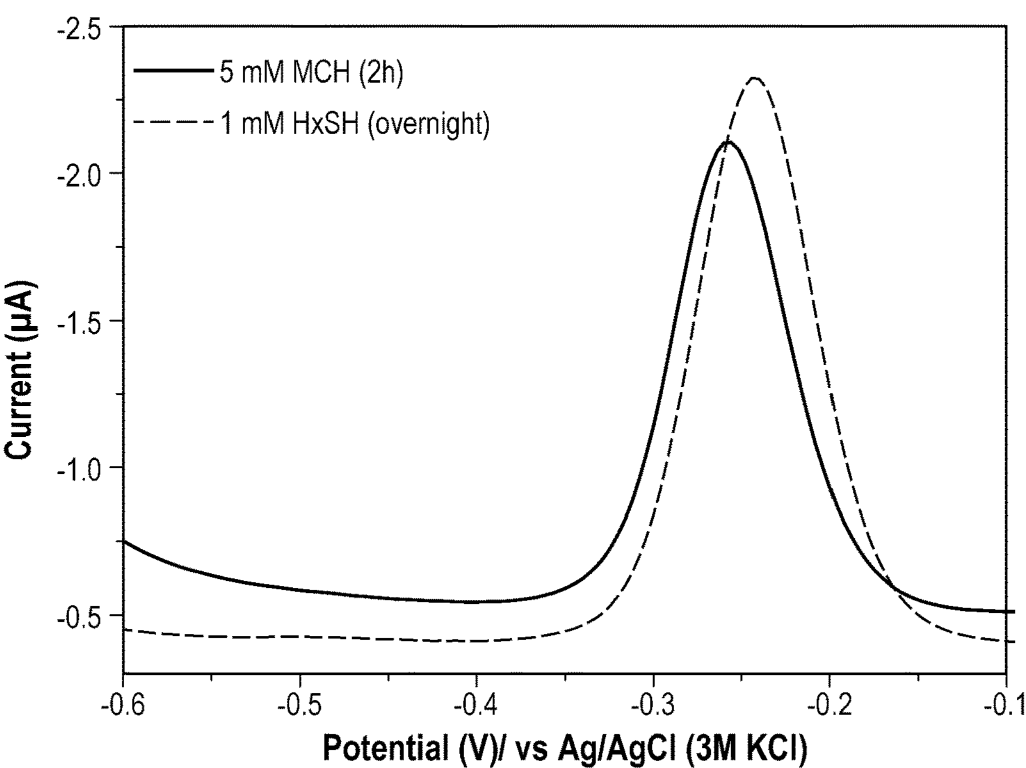
FIG. 3B is a graph showing potential versus current with a curve representing sensing devices incubated in 5 mM MCH for 2 hours and a curve representing sensing devices incubated in 1 mM H×SH.
Figure 3C:
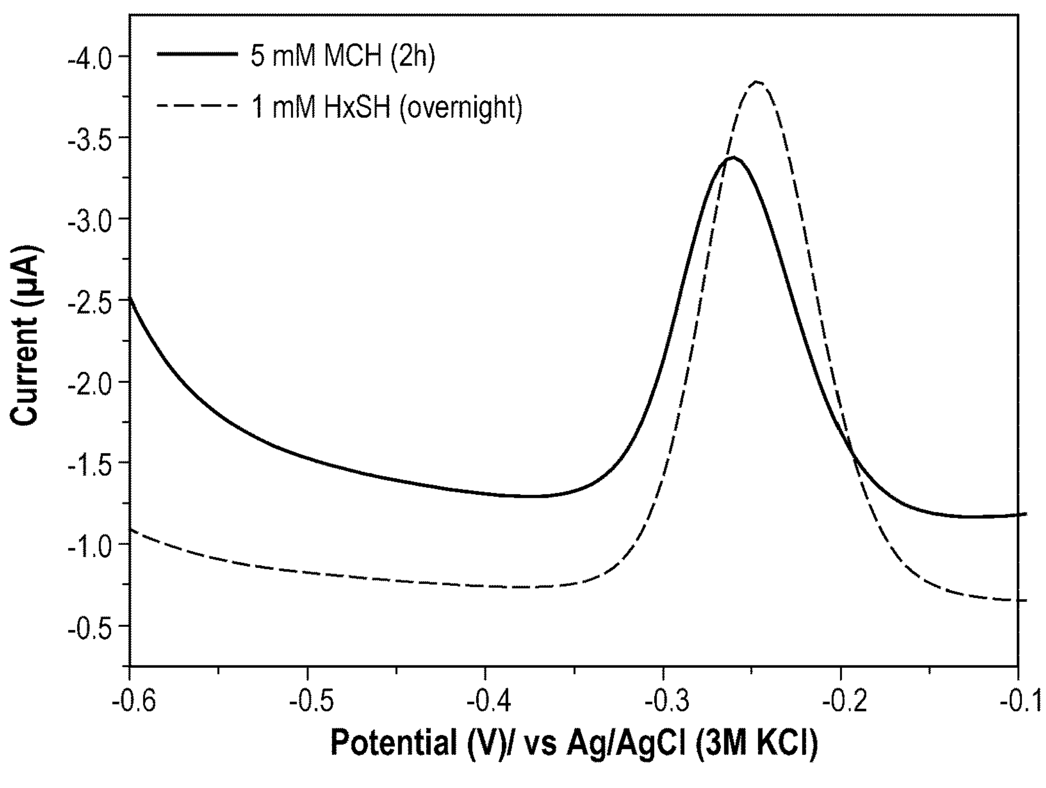
FIG. 3C is a graph showing potential versus current with a curve representing sensing devices incubated in 5 mM MCH for 2 hours and a curve representing sensing devices incubated in 1 mM H×SH.
Figure 3D:
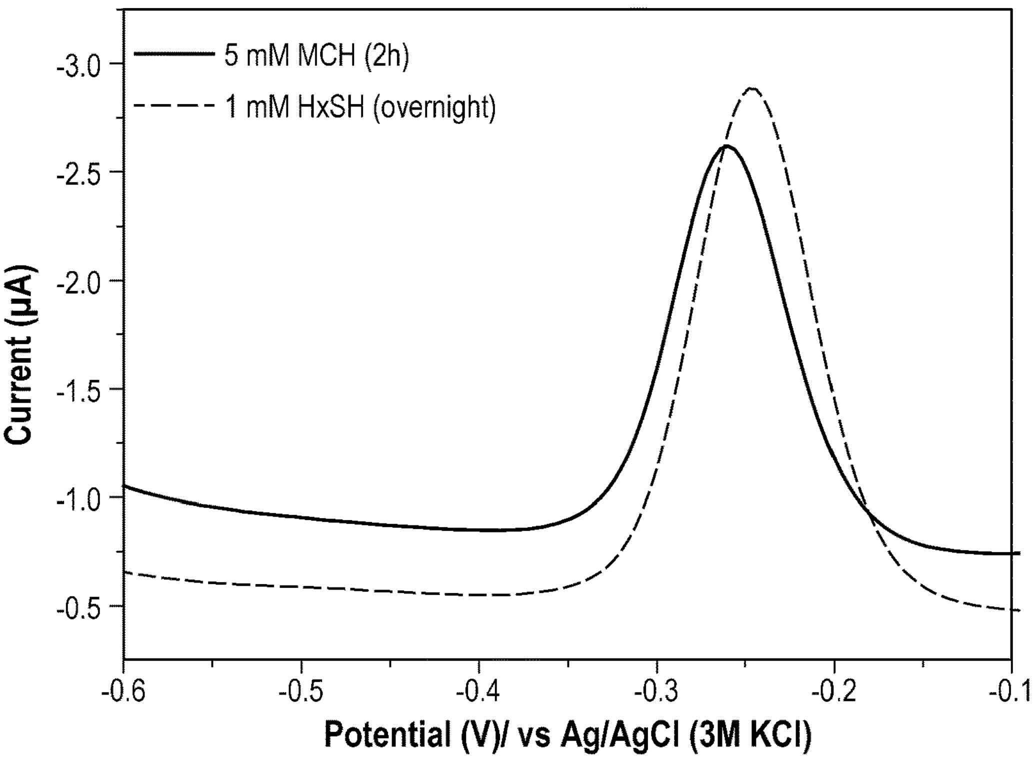
FIG. 3D is a graph showing potential versus current with a curve representing sensing devices incubated in 5 mM MCH for 2 hours and a curve representing sensing devices incubated in 1 mM H×SH.

With further reference to the conventional sensor device 100, FIG. 1B shows a challenge with aptamer sensors, such as the conventional sensor device 100, that is, when placed into initial operation with the sample fluid 130, over a period of 10's of minutes to hours of first use, the signal from the electrode 120 initially decreases by as much as 30%, 50%, or even more. This decrease in signal strength may be due to effects such as fouling by proteins 188, small molecules 186, or other solutes in the sample fluid 130. Alternatively or in addition, this decrease in signal strength may be due to desorption of the sensing monolayer, including aptamer 124 and/or blocking layer 122. The present invention aims to reduce or resolve entirely the amount of initial desorption of the sensing monolayer. During fabrication of a conventional aptamer (see examples section description of standard electrode preparation and incubation for aptamer 124 and blocking layer 122), a portion of the sensing monolayer is physisorbed to the electrode surface 121, or molecules are incorrectly oriented (e.g. blocking layer that is inverted with thiol facing away from electrode 120), or there are portions of the electrode 120 that are physically or electrochemically fragile, or other aspects of the sensing monolayer that can readily detach from the sensor during initial operation. Although an electronic 'burn-in' period could be utilized to stabilize the sensor when in initial use in which a portion of the sensing monolayer is desorbed, such a decrease of the surface concentration of aptamers 124 results in an irrecoverable loss in signal from the sensor device 100, and the decrease of one or more portions of the blocking layer 122 can result in an increase in background current and/or increased electrode 120 fouling, which may result in inaccurate measurements of analyte 180 concentration in the sample fluid 130. This initial trend is visually apparent as described in the examples section.

Methods and devices to cure these, and other, deficiencies of the prior art are disclosed herein. As described above, a method of fabricating an electrochemical aptamer sensor is provided. The method includes incubating an electrode with components that have the ability to constitute a sensing monolayer. The incubating of these components with the electrode results in a sensing monolayer (e.g., aptamers and blocking layer materials) forming and attaching to a surface of the electrode. However, during this incubation and attachment of sensing monolayer to electrode, one or more constituent component may result in being weakly bonded to the electrode. And so, in one embodiment, the sensing monolayer includes at least a plurality of aptamers and at least one weakly bonded constituent. The method then further includes removing the at least one weakly bonded constituent from the sensing monolayer by applying at least one perturbation mechanism to the sensing monolayer while incubating the electrode.

Figure 7:
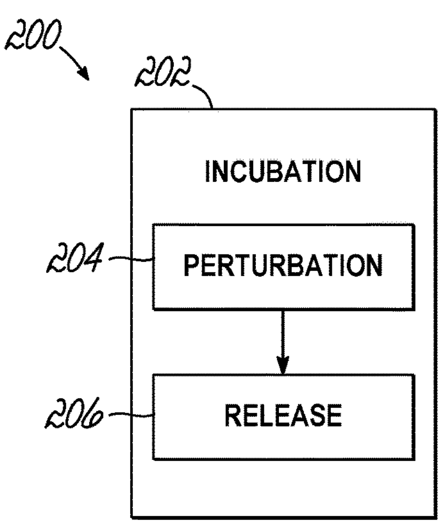
FIG. 7 is a flowchart of a method of incubating an electrochemical aptamer sensor device.

In one example, with reference to FIG. 7, an embodiment of a method 200 in accordance with aspects of the present invention is shown. The method 200 includes incubating 202 an electrode 320 (shown in FIG. 8) for a duration of time in solution.

Figure 8:
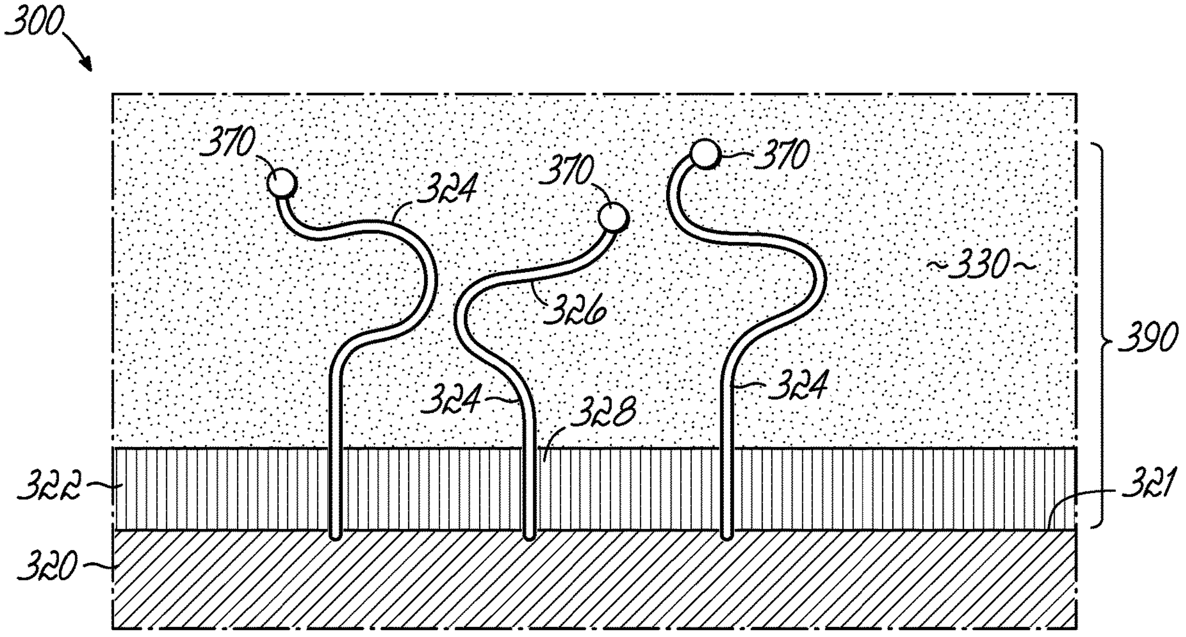
FIG. 8 is a schematic of a sensor device according to the present invention prior to incubation.
Figure 9:
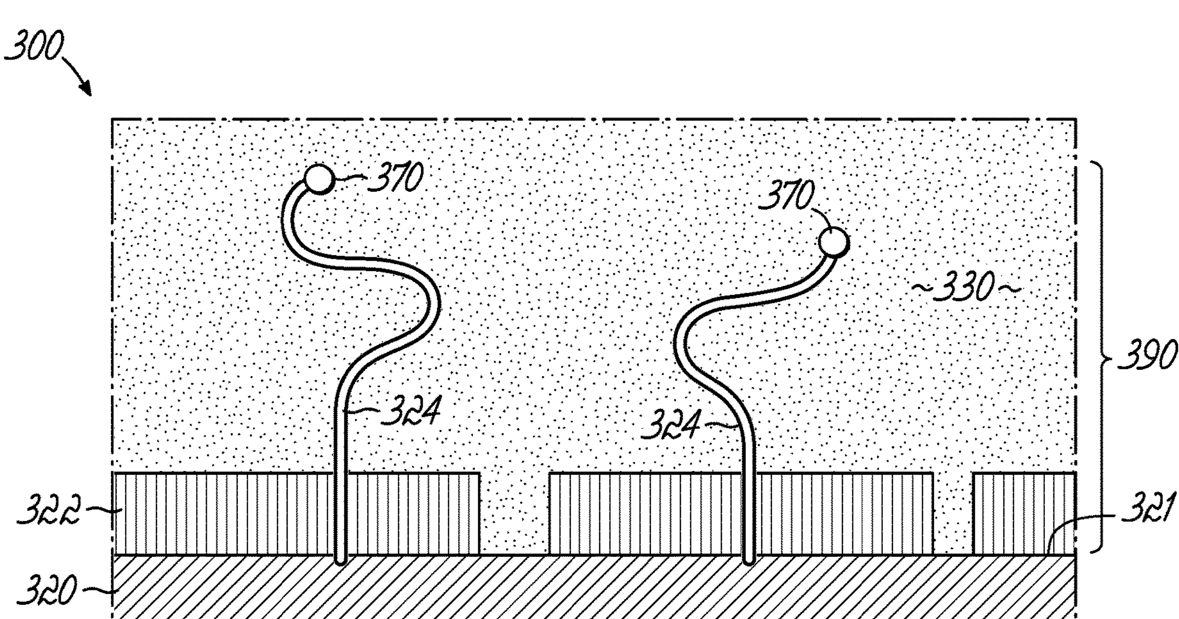
FIG. 9 is a schematic of a sensor device according to the present invention after incubation.

The method 200 further includes a perturbation mechanism 204 step. The perturbation mechanism 204 is applied during the incubation 202 of the sensor device 300, and includes at least one technique to continuously desorb some or all of the sensing monolayer 390 that is weakly or improperly attached to the electrode 320 as illustrated in FIG. 8 and FIG. 9, and therefore clear the electrode 320 for improved attachment of the sensing monolayer to the electrode 320. For example, weakly bonded constituents, such as weakly bonded aptamers 326 or weakly bonded bonding layer portions 328 may be desorbed from the sensing monolayer 390 as a result of the perturbation mechanism 204. The perturbation mechanism 204 may be an electrical mechanism, a mechanical mechanism, a chemical mechanism, a thermal mechanism, or a combination thereof. Particular examples of the perturbation mechanism 204 may include electrical scanning or treatment such as square wave voltammetry, other voltametric techniques, chronoamperometry, ultrasonic agitation, use of a detergent or other agent, or other suitable techniques. Other methods of removing weakly bonded constituents, such as weakly bonded aptamers 326 or weakly bonded bonding layer portions 328, from the sensing monolayer 390 may include sonication or ultrasonication, photoactivation with lasers or lamps to add energy locally or to provide heat to activate desorption, heat itself to activate desorption, electron or ion beam stimulated desorption, or other suitable techniques that remove weakly bonded constituents of the sensing monolayer 390.

Example 2, below, describes a modified method that may be applied to incubation 202 of the sensing monolayer 390 in part or in its entirety (aptamer 324, blocking layer 322, or both). The Examples section, below, describes the resulting performance improvement as a result of the incubation 202 methods of the present invention, clearly showing a reduced initial drop in signal after initial use of the sensor device 300. As a result of the perturbation mechanism 204 being applied to the sensor device 300, weakly bonded constituents, such as such as weakly bonded aptamers 326, weakly bonded blocking layer 322, or weakly bonded bonding layer portions 328, may be desorbed from the sensing monolayer 390 in the release step 206.

Figure 10:
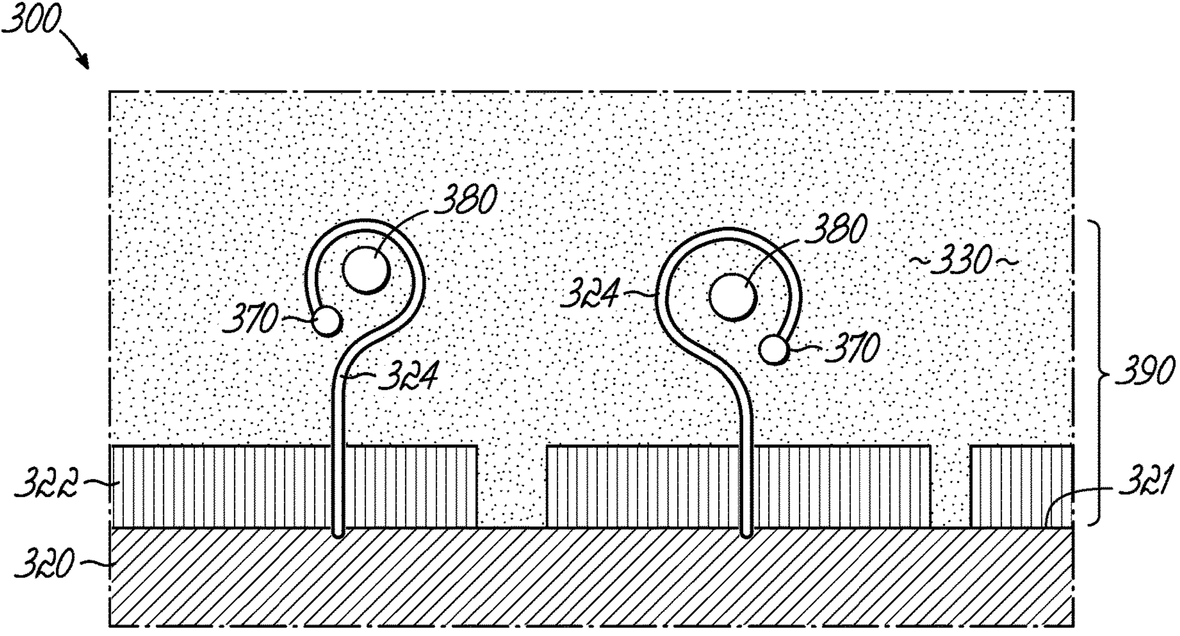
FIG. 10 is a schematic of a sensor device according to the present invention after incubation, and including a fluid sample.

With reference to FIG. 8, a sensor device 300 according to an embodiment of the present invention is shown prior to the sensor device 300 undergoing the method 200 described above and shown in FIG. 7. The sensor device 300 includes at least one electrode 320 which includes a material such as gold, carbon, or other suitable electrode material. The sensor device 300 also includes at least one blocking layer 322 which includes a plurality of molecules such as mercaptohexanol, hexanethiol, peptides, or combinations thereof that may be thiol bonded to the electrode 320, or a plurality of natural solutes, some of which may be found in blood for example, that can act as the blocking layer 322, or other suitable molecules. The specific species of molecules included in the blocking layer 322 may depend on the particular application of the sensor device 300, and on the choice of electrode 320 material. The sensor device 300 further includes at least one aptamer 324 that is responsive to binding to an analyte 380 and which contains a redox tag 170 such as methylene blue. The sensing monolayer 390 may include weakly bonded constituents, such as weakly bonded aptamers 326 or weakly bonded bonding layer portions 328. As shown in FIG. 8, the aptamers 324 and weakly bonded aptamers 326 are a simple stem loop (hairpin) aptamer configured to bond to an analyte 380 (shown in FIG. 10). Other forms of aptamers are acceptable as well, such as those for vancomycin, phenylalanine, or other analytes that are valuable to measure in the body. The bonding of the aptamer 324 to the analyte 380 causes the stem loop to form and the redox current measured from the redox tag 370 to increase, as measured using square wave voltammetry or other suitable technique. In an absence of analyte 380 binding to the aptamer 324, the stem loop conformation does not form, and the redox current would thus not increase. Thus, a measurement of electrical current from the redox tag 370 can be used to interpret changes in the amount of analyte 380 bonded to the aptamer 324, and accordingly related to, for example, the concentration of the analyte 380 in the sample fluid 330 (shown in FIG. 10).

With reference to FIG. 9, the sensor device 300 is shown after the method 200 described above and shown in FIG. 7 is performed. As a result of the perturbation mechanism 204 that occurs during the incubation 202 of the sensor device 300, the weakly bonded constituents of the sensing monolayer 390, such as weakly bonded aptamers 326, weakly bonded blocking layer 322 constituents, or weakly bonded bonding layer portions 328, have been desorbed from the sensing monolayer 390. The desorption of these weakly bonded constituents improves the performance of the sensor device 300 by desorbing weakly bonded portions of the sensing monolayer 390 before use of the sensor device 300. Accordingly, such weakly bonded portions do not affect the sensor device 300 during initial use.

With further reference to embodiments of the present invention and to FIGS. 8 and 9, the weakly bonded portions can be removed and subsequently repaired by either: (a) exposing the sensor 300 to the one or more of the perturbation mechanisms as described herein during incubation of aptamer 324, 326 or layer 322 (e.g. see Example 2); or (b) exposing the sensor 300 to the one or more of the perturbation mechanisms as described herein after incubation of aptamer 324, 326 or layer 322, and then performing an additional incubation of aptamer 324, 326 or layer 322 to repair any locations where weakly bonded portions were removed during the perturbation mechanism. As a result, the final sensor 300 after repair will resemble the sensor 300 of FIG. 8 with a complete layer 322 including aptamers 324, 326. Furthermore, the plurality of molecules attached to the electrode surface may be either weakly bonded or strongly bonded to the electrode surface, and, of the plurality of molecules, at least one of less than 40%, less than 20%, less than 10% or less than 5% of the sensing monolayer are weakly bonded to the electrode surface, verified by measuring the sensor operation at 0 hours (initial use before loss of weakly bonded molecules) and after 24 hours where weakly bonded molecules would be removed, using measures such as microscopy, XPS (x-ray photoelectron spectroscopy), ellipsometry, electrochemical measurements of oxygen reduction current or redox current, electrictrochemical impedance spectroscopy, (electrochemical) quartz crystal microbalance, or other suitable methods used to measure surface density of a monolayer of molecules on an electrode surface.

With further reference to embodiments of the present invention, some electrode 320 materials, such as carbon, can inherently provide a more stable electrode to which aptamers can be covalently bonded using click chemistry, electrodeposition of functionalized polymers or other suitable techniques over alternative electrode materials, such as gold. However, aptamers 324, such as DNA, may readily stick (physisorb) to the surface 321 of carbon based materials. For any electrode 320 material with strong physisorption, the present invention can improve longevity of the electrode 320 as well as improve the sensor device 300 functionality. For example, if most of the aptamer 324 physisorbs, then the physisorbed aptamer 324 will not likely provide a strong response to binding to analyte 380 if the analyte 380 binding is even possible after physisorption of the aptamer 324. Therefore, the present inventions enable a sensor device 300 using aptamers 324 to be fabricated where the aptamers 324 attached to the electrode 320 during incubation 202 are at least one of greater than 30%, 60%, 90%, 95% chemically attached through covalent linkages compared to the total aptamer 324 on the electrode surface 321 (both chemically attached and physisorbed). Even on gold electrodes 320, study of signal degradation over time indicates that weakly bonded aptamers 326 include at least 20% of the total aptamer concentration on the electrode 320, prior to the perturbation mechanism 204 being applied. These same percentages apply to the blocking layer 322 as well. Such blocking layers 322 may include materials such as mercaptohexanol or other blocking layer materials including passivation with natural solutes in serum.

With further reference to embodiments of the present invention, the resulting improved performance of a tested sensor device 300 with the modified incubation 202 step according to the methods 200 of the present invention can be quantified. For example, with the present invention the normalized current measured as peak signal from the redox tag 370 vs. background current decreases over 24 hours by less than one of 3%, 5%, 10%, 20%, 40%, compared to a device tested without benefit of the present invention.

EXAMPLES

Example 1

Chemical repassivation after preliminary scans was analyzed as follows. Electrochemical cleaning of sensor devices according to the present invention was followed by cortisol aptamer incubation for 1 hour in 400 nM of cortisol aptamer. Then, MCH incubation for 2 hours in 5 mM MCH in deionized water was conducted at room temperature. Preliminary scans were done. After these scans, chemical repassivation of the sensor devices in 1 mM MCH/1 mM H×SH was performed overnight. Second round of post-repassivation preliminary scans was performed. Finally, electrochemical testing on the sensor devices was conducted. The data is presented in FIGS. 2A-2D.

FIGS. 2A-2D show graphs of data collected as a result of the incubation method described above tested at a temperature of at least 20 degrees Celcius. The data in FIGS. 2A-2D shows that repassivation according to the present invention improves the quality of the sensing monolayer and it further removes physiosorbed aptamer molecules from the electrode.

FIGS. 3A-3D show graphs of data collected as a result of the incubation method described above tested at a temperature of at least 20 degrees Celcius. Particularly, FIGS. 3A-3D show that repassivation with H×SH increases the peak currents and improves the blocking performance of the blocking layer. FIGS. 3A-3D plot the potential versus current with a curve representing sensing devices incubated in 5 mM MCH for 2 hours and a curve representing sensing devices incubated in 1 mM H×SH. A notable peak shift can be ascribed to the mixed sensing monolayer of the H×SH incubated electrochemical aptamer sensor device in comparison with the MCH incubated electrochemical aptamer sensor device, alone (1st blocking step). Current increase is due to much stronger interaction of H×SH than MCH with aptamer molecules.

Figure 4A:
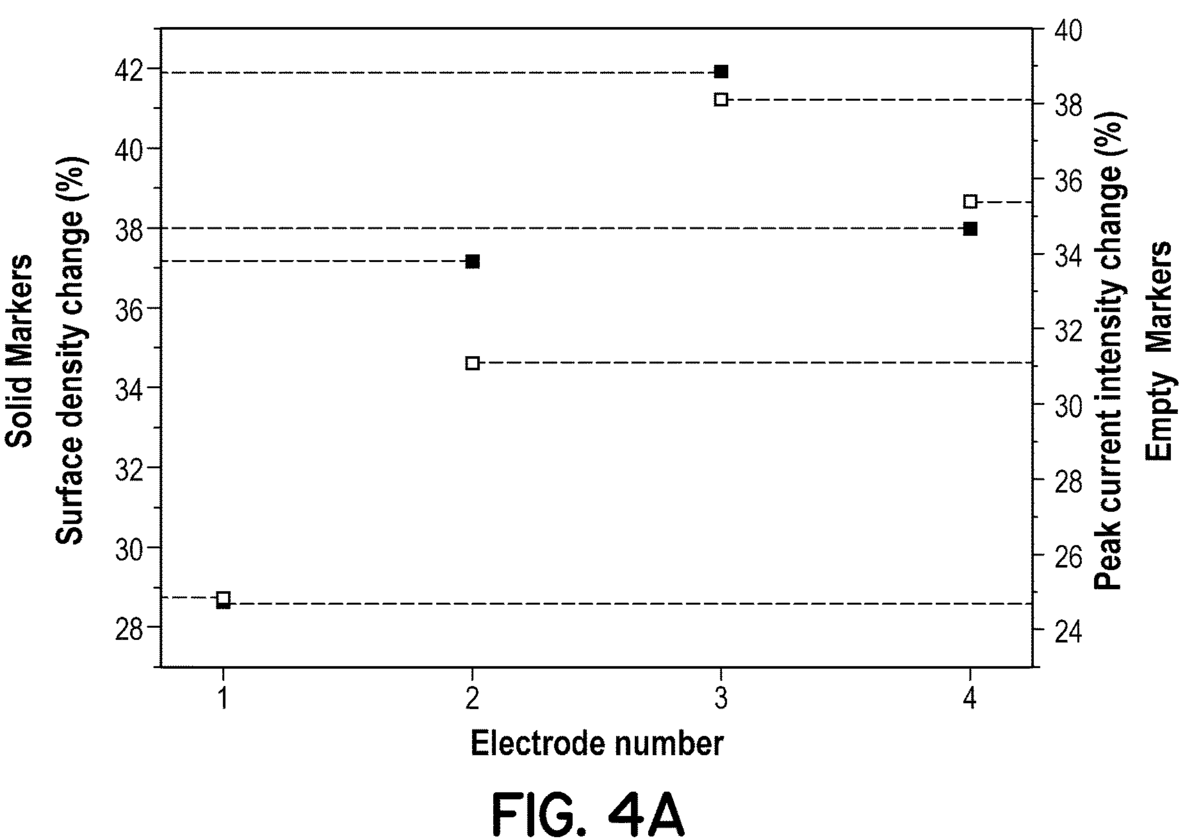
FIG. 4A is a plot showing surface densities of aptamers and/or blocking layer constituents of electrochemical aptamer sensor devices fabricated according to the present invention as well as plotting peak current intensity changes of electrochemical aptamer sensors fabricated according to the present invention.
Figure 4B:
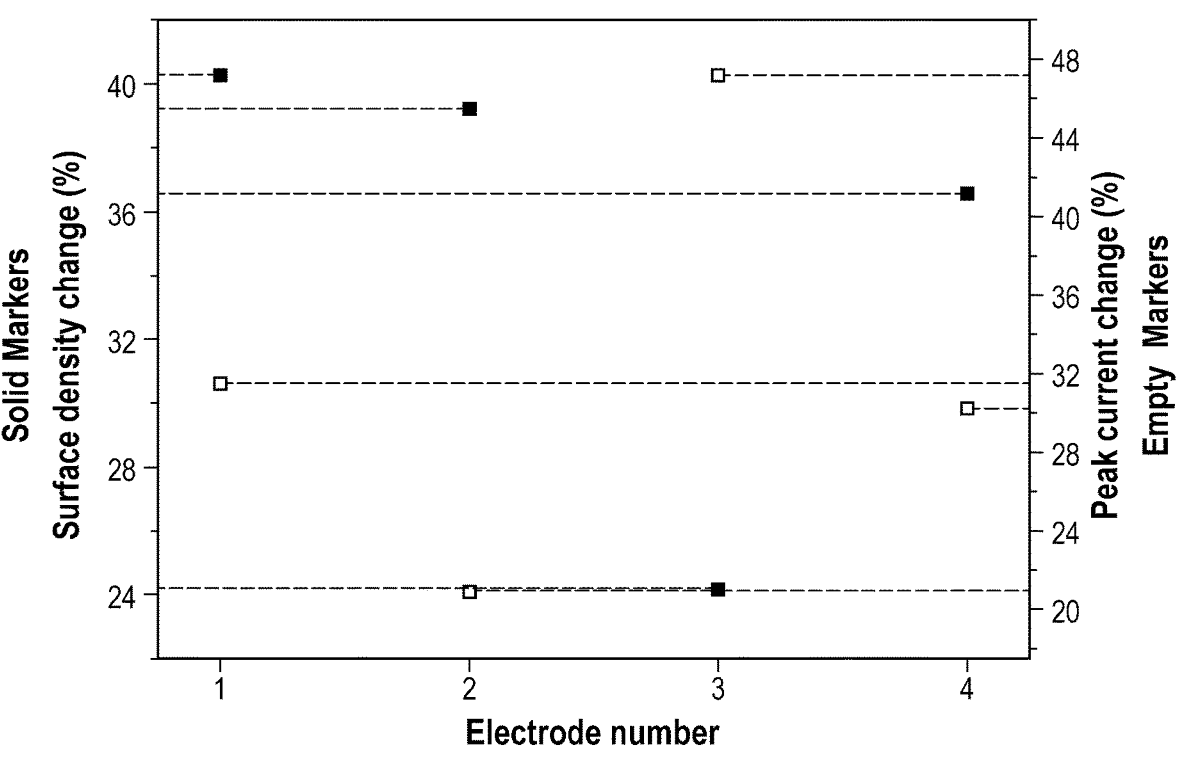
FIG. 4B is a plot showing surface densities of aptamers and/or blocking layer constituents of electrochemical aptamer sensor devices fabricated according to the present invention as well as plotting peak current intensity changes of electrochemical aptamer sensors fabricated according to the present invention.
Figure 4C:
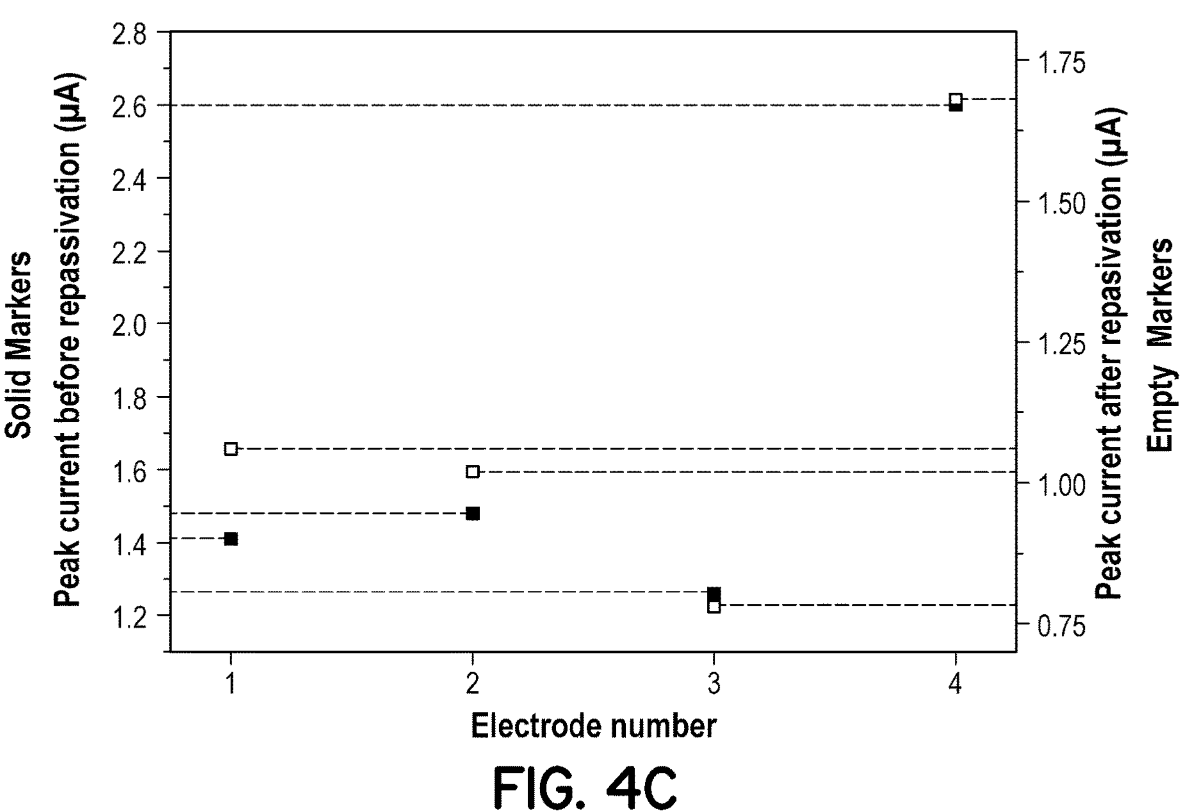
FIG. 4C is a plot showing changes in peak current of electrochemical aptamer sensor devices before and after repassivation of the electrochemical aptamer sensor devices occurs.
Figure 4D:
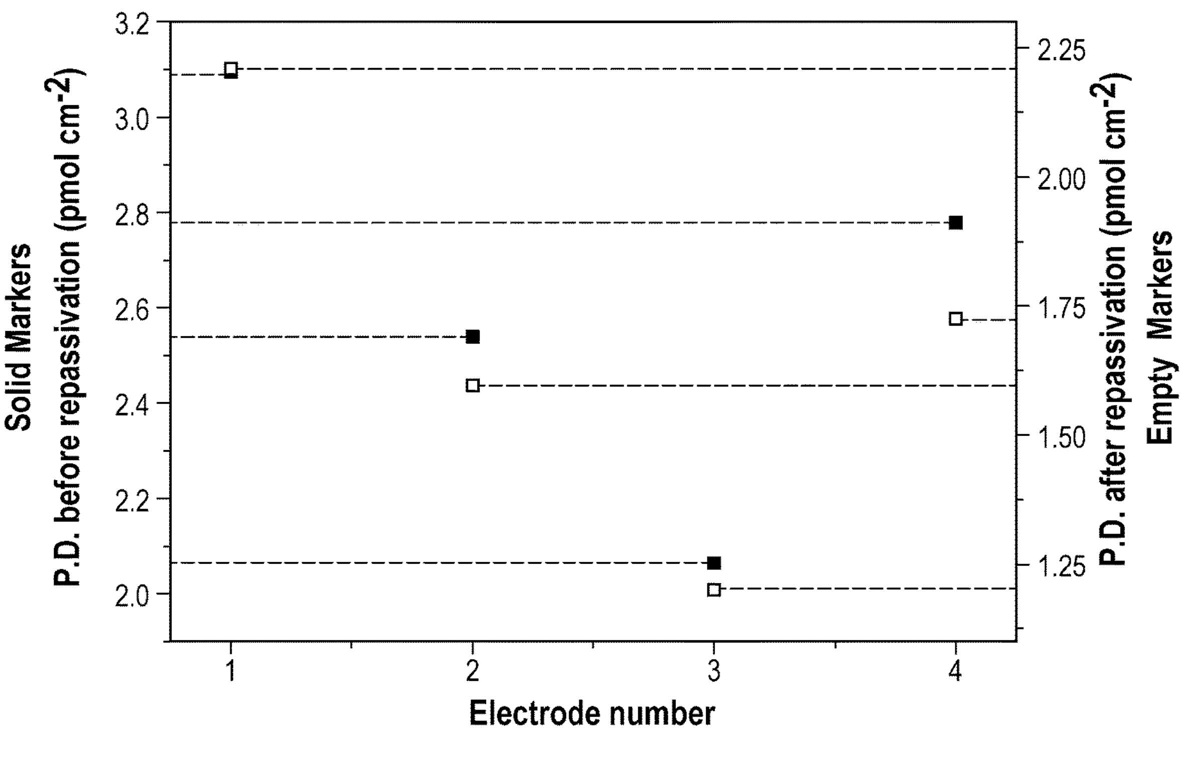
FIG. 4D is a plot showing changes in peak current of electrochemical aptamer sensor devices before and after repassivation of the electrochemical aptamer sensor devices occurs.
Figure 4E:
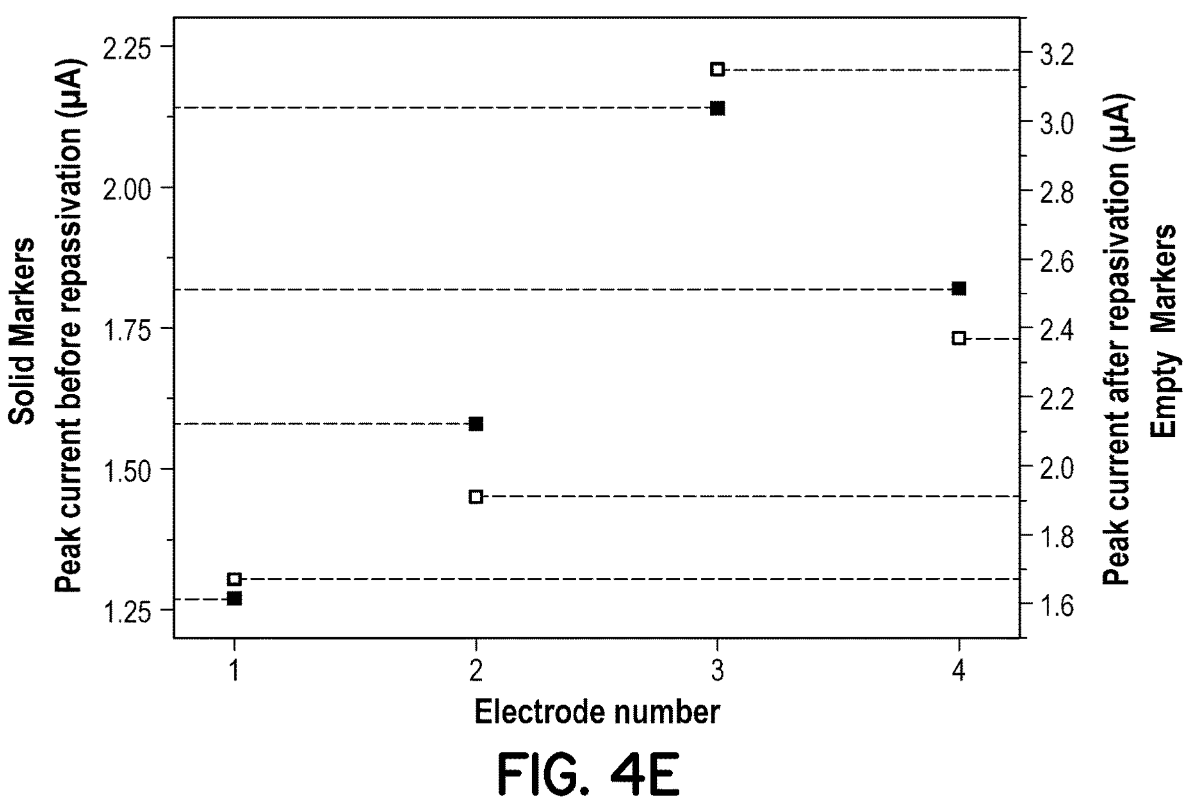
FIG. 4E is a plot showing changes in peak current of electrochemical aptamer sensor devices before and after repassivation of the electrochemical aptamer sensor devices occurs.
Figure 4F:
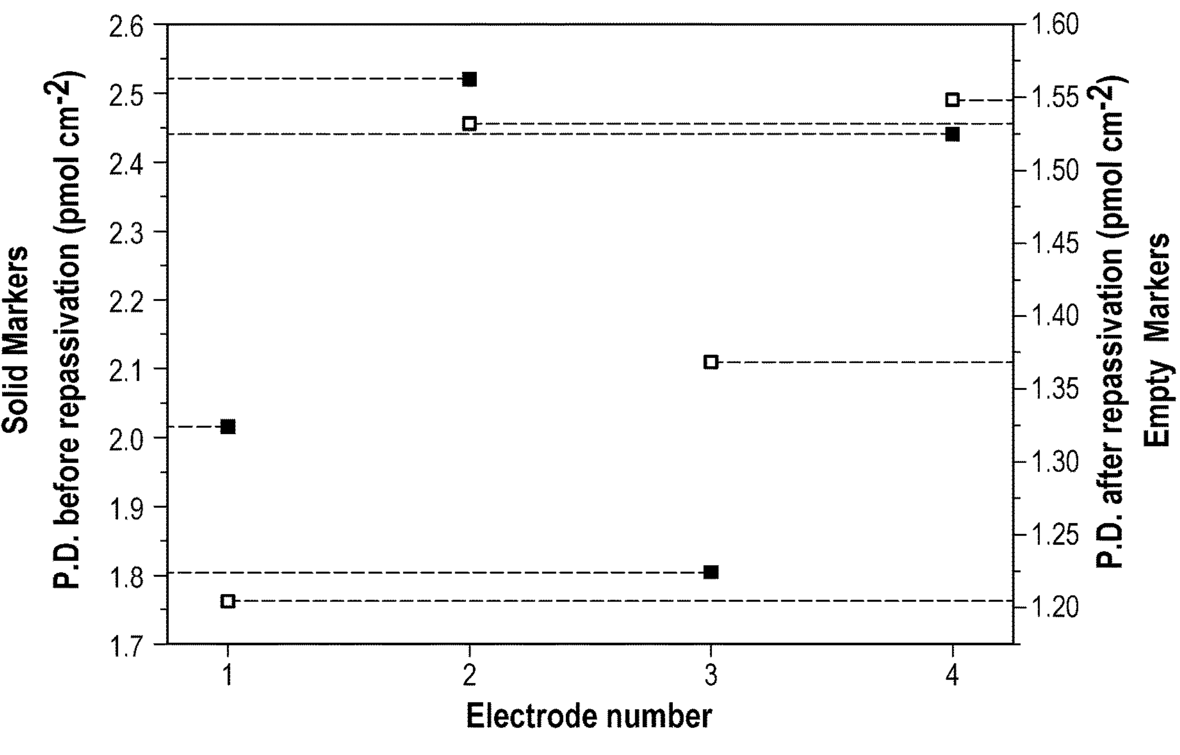
FIG. 4F is plot showing changes in peak current of electrochemical aptamer sensor devices before and after repassivation of the electrochemical aptamer sensor devices occurs.

FIGS. 4A-4F show plots of data confirming changes in characteristics of the electrochemical aptamer sensor devices fabricated by the methods described herein tested at a temperature of at least 20 degrees Celcius. For example, FIGS. 4A-4B confirm that surface densities of aptamers and constituents decrease when subjected to the chemical aptamer sensor fabrication methods described herein, and that peak current intensity increased by various percentages as a result of the electrochemical aptamer sensor fabrication methods described herein. The data in FIGS. 4A-4B shows that all surface densities decreased. FIGS. 4C-4F plot the peak current before repassivation and after repassivation, and accordingly, a difference between these values corresponds to an increase in peak current as a result of the repassivation processes described herein. All electrochemical aptamer sensor devices using MCH currents decreased and all electrochemical aptamer sensor devices using H×SH currents increased This observation tends to show that H×SH interacts with the aptamer in such a way that it brings methylene blue closer to the surface of the electrode.

Example 2

Figure 5:
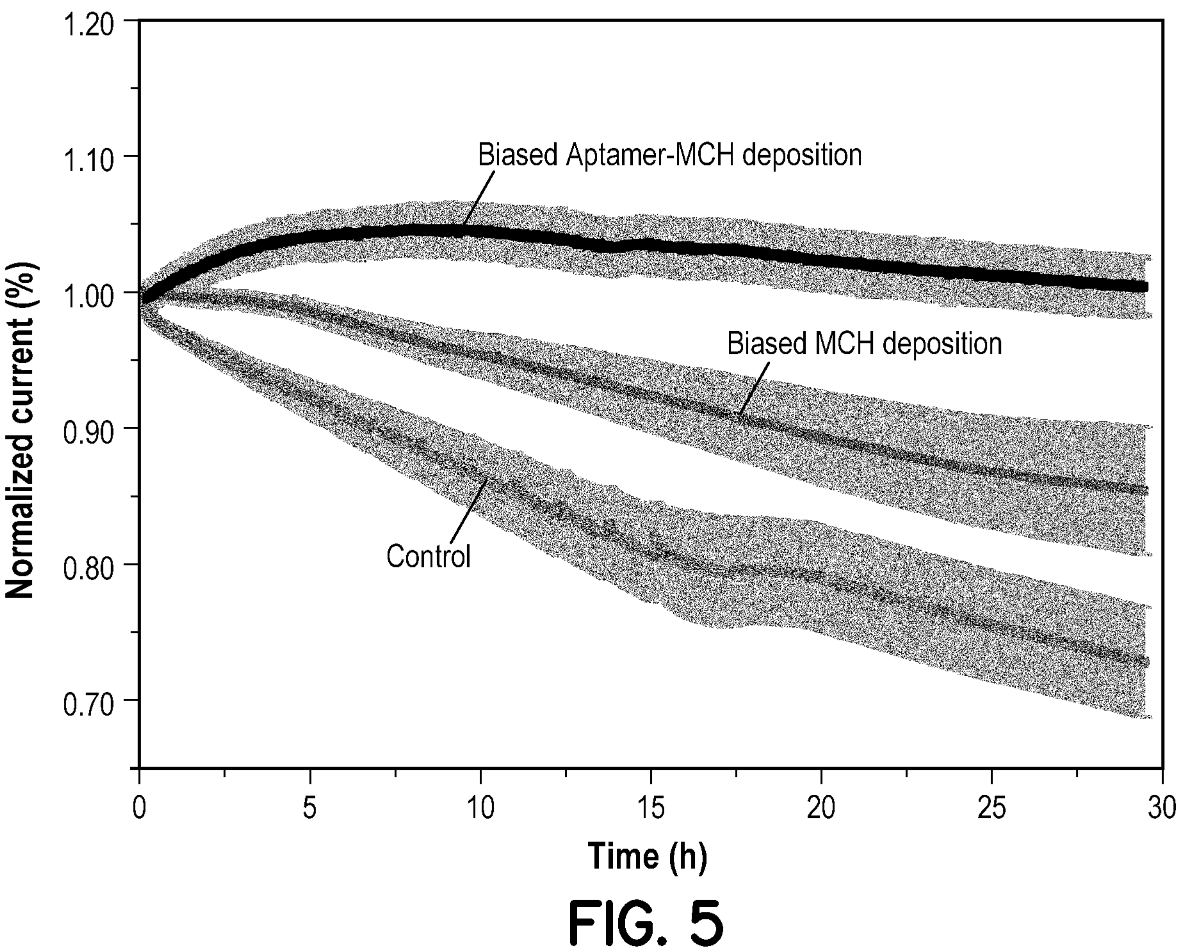
FIG. 5 is a graph showing time versus normalized current of electrochemical aptamer sensor devices using aptamer and MCH incubation under biased conditions.

Aptamer and MCH incubation under biased conditions was analyzed as follows. Electrochemical cleaning of sensors according to the present invention was followed by cortisol aptamer incubation (400 nM; overnight; square wave voltammetry: every 27 s; 120 Hz; Ampl: 35 mV; Step: 1 mV). The sensors were rinsed in DI water. Then, MCH incubation (overnight, 5 mM in 1×PBS water; square wave voltammetry: every 27 s; 120 Hz; Amp: 35 mV; Step: 1 mV) was conducted. The sensors were rinsed again in DI water. Preliminary scans were done. Finally, electrochemical testing on the sensors (min. 18 h) was conducted. The data is presented in FIG. 5 tested at a temperature of at least 20 degrees Celcius.

The data shows that potential biasing during incubation significantly improves the stability of the sensing monolayer by minimizing physisorption and improving the packing density. The mechanism is electrostatic desorption of physiosorbed molecules and weakly bonded portions of the sensing monolayer.

Example 3

Figure 6:
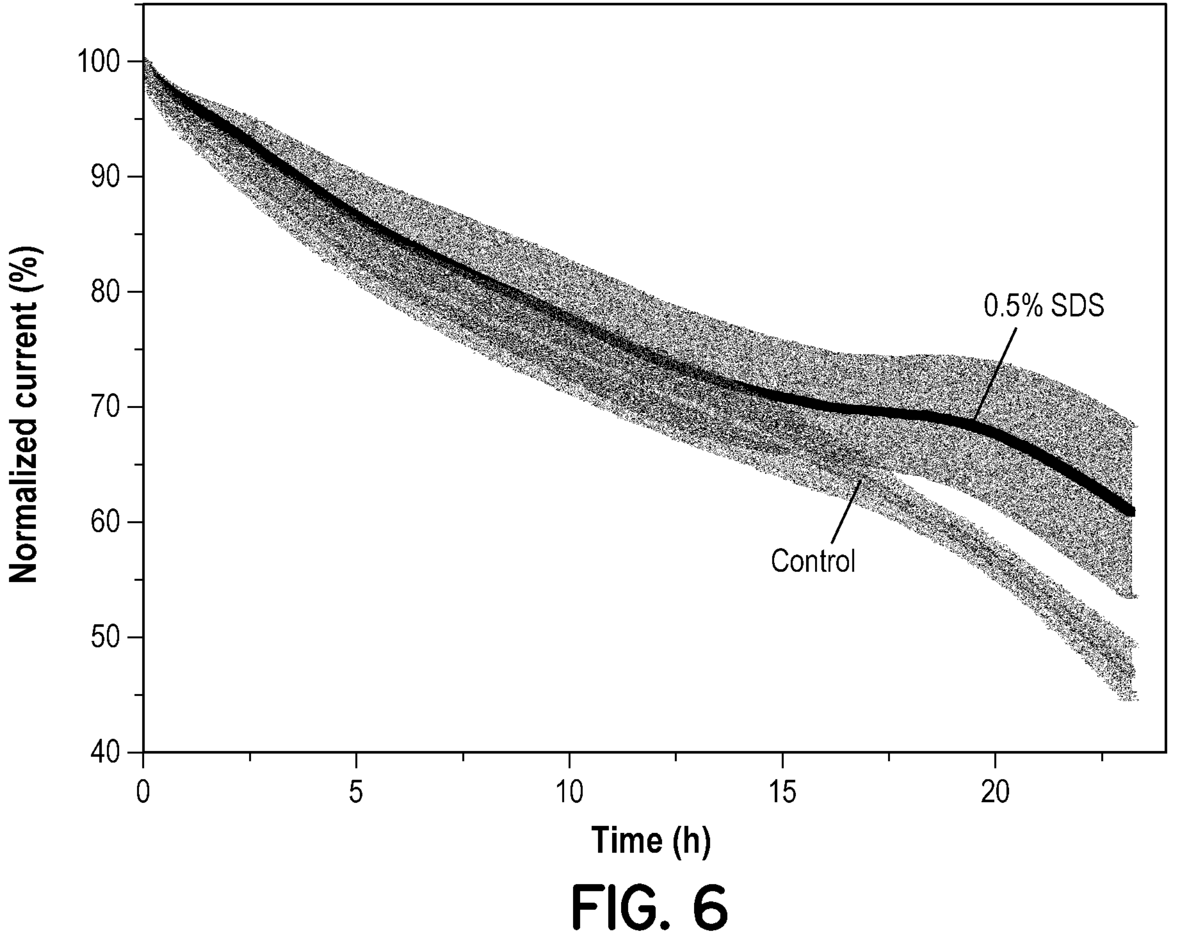
FIG. 6 is a graph showing the influence of the sodium dodecyl sulfate (SDS) treatment vs traditional preparation method.

The influence of the incubation treatment according to the invention as compared to a traditional preparation method was analyzed as follows. Electrochemical cleaning of sensors according to the present invention was followed by cortisol aptamer incubation for 1 hour in 400 nM cortisol aptamer solution. The sensors were rinsed with 25 ml 0.5% SDS prepared in 1×PBS (pH: 7.4); 25 ml of 1×PBS (pH: 7.4); 10 ml DI water. Then, MCH incubation was conducted (overnight, 5 mM in 1×PBS water; rinsing the next day with 25 ml 0.5% SDS; 25 ml of PBS; 10 ml DI water subsequently). Finally, electrochemical testing on the sensors was conducted. The data is presented in FIG. 6 tested at a temperature of at least 20 degrees Celcius.

The data shows that SDS is not powerful enough to remove all physiosorbed aptamer molecules and reach the stability of electrochemically assisted self-assembled monolayer incubation. SDS washing step improved the assembly of the Aptamer-MCH monolayer in comparison with the control group.

Example 4

A method of MCH incubation under square wave voltammetry potential was conducted. Scanning was performed every 4.3 s. Electrochemical cleaning of sensors according to the present invention was followed by cortisol aptamer incubation for 1 hour in 400 nM. Then, MCH incubation was conducted (overnight, 5 mM in 1×PBS buffer (pH: 7.4); square wave voltammetry: every 3.3 s; 120 Hz; Amp: 35 mV; Step: 1 mV). The sensors were rinsed with DI water. Finally, electrochemical testing on the sensors was conducted (min 18 h) tested at a temperature of at least 20 degrees Celcius.

Although not described in detail herein, other steps which are readily interpreted from or incorporated along with the disclosed embodiments shall be included as part of the invention. The embodiments that have been described herein provide specific examples to portray inventive elements, but will not necessarily cover all possible embodiments commonly known to those skilled in the art.

What is claimed is:

1. A method of fabricating an electrochemical aptamer sensor comprising:

incubating an electrode in the presence of components that are adapted to constitute at least a portion of a sensing monolayer, wherein the sensing monolayer includes at least a plurality of aptamers and at least one weakly bonded constituent;

removing the at least one weakly bonded constituent from the sensing monolayer by applying at least one perturbation mechanism to the sensing monolayer while incubating the electrode, or by incubating the electrode then applying at least one perturbation mechanism to the sensing monolayer then incubating the electrode again;

wherein the plurality of aptamers each comprise at least one redox tag, and applying the perturbation mechanism results in a normalized current measured as a peak signal from the redox tag versus a background current decrease over 24 hours that is an amount selected from the group consisting of less than 3%, less than 5%, less than 10%, less than 20%, and less than 40%.

2. The method of claim 1, wherein the perturbation mechanism is selected from the group consisting of an electrical mechanism, a mechanical mechanism, a chemical mechanism, a thermal mechanism, and a combination thereof.

3. The method of claim 1, wherein the sensing monolayer further comprises a blocking layer.

4. The method of claim 3, wherein the blocking layer comprises a material that is an alkythiolate.

5. The method of claim 1, wherein the plurality of aptamers are at least one of greater than 30%, greater than 60%, greater than 90%, or greater than 95% chemically attached to the electrode compared to a total amount of aptamers on the electrode surface via both chemical and physiosorbed attachment.

6. An electrochemical aptamer sensor comprising:

an electrode having an electrode surface;

a sensing monolayer, the sensing monolayer comprising at least a plurality of molecules forming the sensing monolayer, the sensing monolayer attached to the electrode surface;

wherein the plurality of molecules attached to the electrode surface may be either weakly bonded or strongly bonded to the electrode surface;

and wherein, of the plurality of molecules, at least one of less than 40%, less than 20%, less than 10% or less than 5% of the sensing monolayer are weakly bonded to the electrode surface.

7. The sensor of claim 6, wherein at least a portion of the molecules are aptamers.

8. The sensor of claim 6, wherein at least a portion of the molecules form a blocking layer.

9. A method of fabricating an electrochemical aptamer sensor comprising:

incubating an electrode in the presence of components that are adapted to constitute at least a portion of a sensing monolayer, wherein the sensing monolayer includes at least a plurality of aptamers and at least one weakly bonded constituent;

removing the at least one weakly bonded constituent from the sensing monolayer by applying at least one perturbation mechanism to the sensing monolayer while incubating the electrode, or by incubating the electrode then applying at least one perturbation mechanism to the sensing monolayer then incubating the electrode again;

wherein the plurality of aptamers are at least one of greater than 30%, greater than 60%, greater than 90%, or greater than 95% chemically attached to the electrode compared to a total amount of aptamers on the electrode surface via both chemical and physiosorbed attachment.

10. The method of claim 9, wherein the perturbation mechanism is selected from the group consisting of an electrical mechanism, a mechanical mechanism, a chemical mechanism, a thermal mechanism, and a combination thereof.

11. The method of claim 9, wherein the sensing monolayer further comprises a blocking layer.

12. The method of claim 11, wherein the blocking layer comprises a material that is an alkythiolate.

* * * * *